United States Patent [19]

Gupta et al.

[11] Patent Number: 5,512,550
[45] Date of Patent: Apr. 30, 1996

[54] METHOD FOR INHIBITING ANGIOGENESIS WITH MODIFIED PLATELET FACTOR-4 AND CLEAVED PLATELET FACTOR-4

[75] Inventors: Shalley K. Gupta, Indianapolis; Jai P. Singh, Carmel, both of Ind.

[73] Assignee: Eli Lilly and Company, Indianapolis, Ind.

[21] Appl. No.: 439,546

[22] Filed: May 11, 1995

Related U.S. Application Data

[62] Division of Ser. No. 952,797, Sep. 25, 1992, abandoned.

[51] Int. Cl.$^6$ ............. A61K 38/36; C07K 14/745; C12P 21/06
[52] U.S. Cl. ............. 514/12; 514/2; 530/380; 530/300; 435/69.6
[58] Field of Search ............ 514/2, 12; 530/380, 530/300; 435/69.6

[56] References Cited

U.S. PATENT DOCUMENTS

| | | | |
|---|---|---|---|
| 4,645,828 | 2/1987 | Twardzik et al. | 530/324 |
| 4,737,580 | 4/1988 | Twardzik et al. | 530/388 |
| 4,844,895 | 7/1989 | Thorbecke et al. | 424/88 |
| 5,086,164 | 2/1992 | Maione et al. | 530/324 |
| 5,112,946 | 5/1992 | Maione | 530/324 |

OTHER PUBLICATIONS

R. Eisman, et al., *Blood*, vol. 76, No. 2, pp. 336–344 (1990).
M. Y. Stoeckle, et al., *The New Biologist*, vol. 2, No. 4, pp. 313–323 (1990).
T. Maione, et al., *Science*, vol. 247, pp. 77–79, Inhibition of Angiogenesis by Recombinant Human Platelet Factor–4 and Related Peptides, Jan. 5, 1990.
C. J. Green, et al., *Molecular and Cellular Biology* vol. 9, No. 4, pp. 1445–1451, (1989).
A. Walz et al., *Biochemical and Biophysical Research Communications*, vol. 159, No. 3, pp. 969–975 (1989).
M. Poncz, et al., *Blood*, vol. 69, No. 1, pp. 219–223, (1987).

*Primary Examiner*—Robert A. Wax
*Assistant Examiner*—K. Cochrane Carlson
*Attorney, Agent, or Firm*—Ronald S. Maciak; James P. Leeds; David E. Boone

[57] ABSTRACT

The present invention is based of the discovery of two modified forms of human platelet factor-4, herein named MPF-4 and CPF-4, which were isolated from serum free culture medium of lipopolysaccharide-stimulated peripheral blood leukocytes. Amino acid sequence determination revealed that MPF-4 shares homology with platelet factor-4 beginning at N-terminal residue 17. CPF-4 consists of MPF-4 disulfide bonded to the 16 N-terminal residues of platelet factor-4. Both MPF-4 and CPF-4 are potent inhibitors of endothelial cell proliferation, approximately 10–100 fold more potent than native or recombinant platelet factor-4, making them useful in the treatment of angiogenic diseases.

2 Claims, 1 Drawing Sheet

METHOD FOR INHIBITING ANGIOGENESIS WITH MODIFIED PLATELET FACTOR-4 AND CLEAVED PLATELET FACTOR-4

This application is a division, of application Ser. No. 07/952,797, filed Sep. 25, 1992, now abandoned.

BACKGROUND OF THE INVENTION

The present invention is based on the discovery of a new N-terminal region processed form of human platelet factor-4, hereinafter modified platelet factor-4 (MPF-4). The invention also includes a proteolytically cleaved, non-reduced form of platelet factor-4, hereinafter cleaved platelet factor-4 (CPF-4). Both MPF-4 and CPF-4 may be isolated from the spent culture medium of lipopolysaccharide-stimulated peripheral blood leukocytes (PBLs).

Amino acid sequencing revealed that MPF-4 is homologous to platelet factor-4, (PF-4) beginning with Ser-17 and thus is presumed to be a naturally-occurring cleavage product of PF-4. CPF-4 bears the same amino acid sequence as PF-4 but differs in that the peptide bond between residues 16 and 17 is absent. However, the two resulting peptides remain bonded via disulfide bridges. Most significantly, the compounds of the present invention are potent inhibitors of endothelial cell proliferation and are anywhere from 10–100 fold more active than native PF-4, depending on the source of PF-4 and the reporting laboratory.

PF-4 is the prototype member of a growing family of small inducible proteins that are released from various cell types after stimulation with mitogens or cytokines. This family of proteins, known as "intercrines," has been found to modulate a variety of biological processes such as angiogenesis, cell proliferation, coagulation, inflammation, and tissue repair. See Oppenheim et al., Properties of the Novel Proinflammatory Supergene "Intercrine" Cytokine Family, *Ann, Rev, Immunol.* 9: 617–648, 1991; Taylor et al., Protamine is an Inhibitor of Angiogenesis, *Nature* 297: 307–312, 1982; and Maione et al., Inhibition of Angiogenesis by Recombinant Human Platelet Factor-4 and Related Peptides, *Science* 247: 77–79, 1990).

Other members of the intercrine family include interluekin-8 (IL-8), melanocyte growth stimulating activity (hGro/MGSA), β-thromboglobulin (β-TG), neutrophil activating protein (NAP-2), IP-10, and macrophage inflammatory protein (MIP-2). See Lindley et al., Synthesis and Expression in *Escherichia coil* of the Gene Encoding Monocyte-derived Neutrophil-Activating Factor: Biological Equivalence between Natural and Recombinant Neutrophil-activating Factor, *Proc. Natl. Acad. Sci*, 85: 9199–9203, 1988; Walz et al., A Novel Cleavage Product of B-Thromboglobulin Formed in Cultures of Stimulated Mononuclear Cells Activates Human Neutrophils, *Biochem, Biophys. Res. Commun*, 159: 969–975, 1989; Luster et al., Gamma-interferon Transcriptionally Regulates an Early Response Gene Containing Homology to Platelet Proteins, *Nature* 315: 672–676, 1985; and Wolpe et al., Identification and Characterization of Macrophage Inflammatory Protein 2, *Proc. Natl. Acad. Sci*, 86: 612–616, 1989).

The complete primary structure of PF-4 is well known in the art (Poncz et al., Cloning and Characterization of Platelet Factor 4 cDNA Derived from a Human Erythroleukemic Cell Line, *Blood* 69: 219–223, 1987. Analogs and fragments of PF-4 are also well known and have been referred to as "Oncostatin-A in U.S. Pat. Nos. 4,645,828 and 4,737,580, herein incorporated by reference. Studies have shown that the intercrine family of proteins contain a characteristic cysteine-X-cysteine (CXC) motif located in the N-terminal region. The CXC motif participates in producing the secondary and tertiary structure of native PF-4 via formation of intramolecular disulfide bonds with residues Cys-36 and Cys-51 (St. Charles es al., The Three-dimensional Structure of Bovine Platelet Factor 4 at 3.0-A Resolution, *J. Biol. Chem*, 264: 2092–2098, 1989).

Moreover, based on the published three dimensional structure of bovine PF-4, it was determined that N-terminal residues Gln-9 to Val-19 form a large open loop and that Thr-16 hydrogen bonds to Cys-51. These N-terminal structures have been shown to be important for the immunoregulatory activity of PF-4 (Katz et al., Protease-induced Immunoregulatory Activity of Platelet Factor 4, *Proc. Natl. Acad. Sci.* 83: 3491–3495, 1986).

Although PF-4 is mainly found within the alpha-granules of platelets, genomic cloning has revealed evidence for duplication of the human PF-4 gene producing alternative forms of PF-4, namely PF-4varI and PF-4alt (Doi, et al., Structure of the Rat Platelet Factor 4 Gene: A Marker for Magakaryocyte Differentiation, *Mol. Cell Biol.* 7: 898–912. 1987). The deduced amino acid sequence of the variants shows important differences in the N-terminal leader sequence and in the lysine-rich C-terminal domain (Green et al., Identification and Characterization of a Human Gene Variant of Platelet Factor 4, *Mol. Cell. Bio.* 9: 1445–1451, 1989; Eisman et al., Structural and Functional Comparison of the Genes for Human Platelet Factor 4 and PF-4alt, *Blood* 76: 336–344, 1990). The changes in the leader sequence suggests a difference in its mode of secretion and the tissue type where it is expressed. Thus, the alternate forms of PF-4 may also be produced by cells other then platelets.

It is also well known that the lysine rich C-terminal region of PF-4 strongly binds to heparin and related glycosaminoglycans (Rucinski et al., Human Platelet Factor 4 and its C-terminal Peptides: Heparin Binding and Clearance from the Circulation, *Thrombos, Haemestas*. 63: 493–498, 1990).

Mutant forms of PF-4 have been disclosed as have methods of using the mutants for treating angiogenic diseases. See U.S. Pat. Nos. 5,086,164 and 5,112,946, herein incorporated by reference. These patents teach PF-4 modifications made in the C-terminal region resulting in analogs that no longer have heparin-binding capacity. The present invention discloses MPF-4 and CPF-4 which are processed forms of PF-4.

Finally, currently held beliefs in medical science state that angiogenesis is required for solid tumors to grow beyond several cubic centimeters. Therefore, the use of angiogenic inhibitors such as MPF-4 and CPF-4 presents a potentially viable approach for the treatment of solid tumors.

SUMMARY OF THE INVENTION

The present invention includes a composition of MPF-4 consisting essentially of a protein having the amine acid sequence of SEQ ID. NO: 1, and a composition of CPF-4 consisting essentially of a protein having the amine acid sequence of SEQ ID NO: 1 disulfide bonded to a protein having the amine acid sequence of SEQ ID NO: 2. The disulfide bonds bridge the two protein chains of CPF-4 from Cys-20 of SEQ ID NO: 1 to Cys-10 of SEQ ID NO: 2 and Cys-36 of SEQ ID NO: 1 to Cys-12 of SEQ ID NO: 2. The invention also includes methods for purifying HPF-4 and CPF-4 comprising reversed phase chromatography followed by heparin affinity chromatography followed by reversed phase chromatography. Additionally, a method of inhibiting angiogenesis which comprises administering an inhibitory amount of HPF-4 or CPF-4 is claimed.

DETAILED DESCRIPTION OF THE INVENTION

Figure 1:
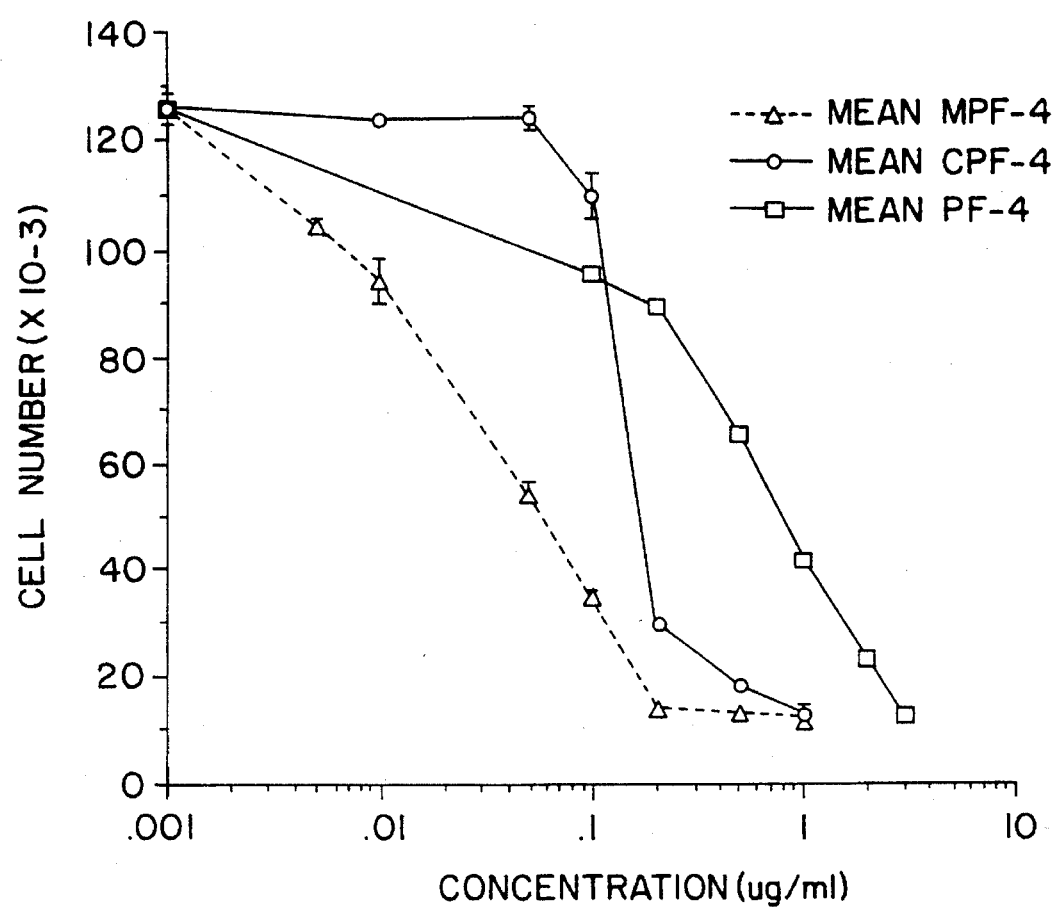
FIG. 1 is a concentration effect graph showing the inhibition of endothelial cell proliferation by MPF-4, CPF-4 and PF-4.

MPF-4 is a naturally-occurring protein composed of 54 amine acid residues and has a molecular weight of about 7 kilodaltons as determined by SDS PAGE. MPF-4 is 100% homologous with the 54 C-terminal residues of PF-4 and is thus believed to be a processed form of PF-4. The amine acid sequence of MPF-4 is set forth in SEQ. ID. NO: 1.

CPF-4 is a naturally-occurring protein composed of a 16 amino acid chain (SEQ. ID. NO: 2) and the 54 amino acid chain of MPF-4 (SEQ. ID. NO: 1). CPF-4 has a molecular weight of about 7.8 to 8.0 kilodaltons as determined by SDS PAGE. The two protein chains of CPF-4 are disulfide bonded between Cys-20 of SEQ. ID. NO: 1 and Cys-10 of SEQ. ID. NO: 2. another disulfide bond bridges Cys-36 of SEQ. ID. NO: 1 to Cys-12 of SEQ. ID. NO: 2.

The ordinarily skilled artisan will understand that some conservative amino acid substitutions can be made to these sequences without adversely affecting the invention. Conservative amino acid substitutions include interchanges between Gly and Ala, Asp and Glu, Asn and Gln, Phe and Tyr, and Lys and Arg.

Like the parent protein, both MPF-4 and CPF-4 bind heparin and inhibit endothelial cell growth making them attractive candidates for therapeutic use in treating angiogenic and cell poliferative diseases. The heparin binding domain is believed to be Lys-45 through Lys-50 of SEQ ID NO: 1:

Given the sequence information herein disclosed and the state of the art in solid phase protein synthesis, essentially pure MPF-4 and CPF-4 can be obtained via chemical synthesis. The principles of solid phase chemical synthesis of polypeptides are well known in the art and may be found in general texts in the area such as Dugas, H. and Penney, C., *Bioorganic Chemistry* (1981) Springer-Verlag, New York, pgs. 54–92.

For example, peptides or proteins such as MPF-4 may be synthesized by solid-phase methodology utilizing an Applied Biosystems 430A peptide synthesizer (Applied Biosystems, Inc., 850 Lincoln Center Drive, Foster City, Calif. 94404) and synthesis cycles supplied by Applied Biosystems. Boc amino acids and other reagents are commercially available from Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asparagine, Glutamine, and Arginine are coupled using preformed hydroxy benzotriazole esters. The following side chain protecting groups may be used:

Arg, Tosyl
Asp, cyclohexyl
Glu, cyclohexyl
Ser, Benzyl
Thr, Benzyl

Tyr, 4-bromo carbobenzoxy

Boc deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at zero degrees centigrade or below, preferably −20° C. for thirty minutes followed by thirty minutes at 0° C. After removal of the HF, the peptide/resin is washed with ether, and the peptide extracted with glacial acetic acid and lyophilized.

Likewise, the state of the art in molecular biology provides the ordinarily skilled artisan another means by which essentially pure MPF-4 and CPF-4 can be obtained. Although both molecules may be produced by solid phase peptide synthesis, isolation from spent culture medium, or recombinant methods, recombinant methods are preferred if a high yield is desired. The basic steps in the recombinant production of either MPF-4 of CPF-4 include:

a) isolation of a natural DNA sequence encoding MPF-4 or through the construction of a synthetic or semi-synthetic DNA coding sequence, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of MPF-4 or CPF-4, and e) recovering and purifying the recombinantly produced proteins and (if necessary) refolding the protein to its native conformation.

As previously stated, the coding sequences for the two proteins may be wholly synthetic or the result of modification to the larger, native PF-4-encoding DNA. A DNA sequence that encodes native PF-4 is described in U.S. Pat. No. 5,086,164 and may be used as starting material in the recombinant production of MPF-4 or precursor proteins by altering the native sequence to achieve the desired results.

Synthetic genes, the in vitro or in vivo transcription and translation of which will result in the production of either MPF-4 or CPF-4, may be constructed by techniques well known in the art. Owing to the natural degeneracy of the genetic code, the skilled artisan will recognize that a sizable yet definite number of DNA sequences may be constructed which encode either MPF-4 or CPF-4.

The methodology of synthetic gene construction is well known in the art. See Brown, et al. (1979) *Methods in Enzymology*, Academic Press, N.Y., Vol. 68, pgs. 109–151. DNA sequences that encode either MPF-4 or CPF-4 may be designed based on the amino acid sequences herein disclosed and the published PF-4 DNA sequence. Once designed, the sequence itself may be generated using conventional DNA synthesizing apparatus such as the Applied Biosystems Model 380A or 380B DNA synthesizers (Applied Biosystems, Inc., 850 Lincoln Center Drive, Foster City, Calif. 94404).

To effect the expression of either MPF-4 or CPF-4, one inserts the engineered synthetic DNA sequence in any one of many appropriate recombinant DNA expression vectors through the use of appropriate restriction endonucleases. See generally Maniatis et al. (1989) *Molecular Cloning; A Laboratory Manual*, Cold Springs Harbor Laboratory Press, N.Y., Vol. 1–3. Restriction endonuclease cleavage sites are engineered into either end of the MPF-4-encoding DNA to facilitate isolation from and integration into known amplification and expression vectors. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein of interest. The coding sequence must be positioned so as to be in proper reading frame with the promoter and ribosome binding site of the expression vector, both of which are functional in the host cell in which the protein is to be expressed.

So as to achieve efficient transcription of the synthetic gene, said gene must be operably associated with a promoter-operator region. Therefore, the promoter-operator region of the synthetic gene is placed in the same sequential orientation with respect to the ATG start codon of the synthetic gene.

A variety of expression vectors useful for transforming prokaryotic and eukaryotic cells are well known in the art. see *The Progmea Biological Research Products Catalogue* (1992) (Promega Corp., 2800 Woods Hollow Road, Madison, Wis, 53711–5399); and *The Stratagene Cloning Systems Catalogue* (1992) (Stratage Corp., 11011 North Torrey Pines Road, La Jolla, Calif., 92037). Also, U.S. Pat. No. 4,710,473 describes circular DNA plasmid transformation vectors useful for expression of exogenous genes. in *E. coli* at high levels. These plasmids are useful as transformation vectors in recombinant DNA procedures and a) confer on the plasmid the capacity for autonomous replication in a host cell;

b) control autonomous plasmid replication in relation to the temperature at which host cell cultures are maintained;

c) stabilize maintenance of the plasmid in host cell populations;

d) direct synthesis of a protein prod. indicative of plasmid maintenance in a host cell population;

e) provide in series restriction endonuclease recognition sites unique to the plasmid; and f) terminate mRNA transcription.

These circular DNA plasmids are useful as vectors in recombinant DNA procedures for securing high levels of expression of exogenous genes.

Having constructed an expression vector, the next step is to place the vector into a suitable cell and thereby construct a recombinant host cell useful in the expression of the gone of interest. Techniques for transforming cells with recombinant DNA vectors are well known in the art and may be found in such general references as Maniatis, el al. supra. Host cells made be constructed from either eukaryotic or prokaryotic cells. Eukaryotic host cells are capable of carrying out posttranslational glycosylations on expressed proteins and some are capable of secreting the desired protein into the culture medium.

Prokaryotic host cells generally produce the protein at higher rates, are easier to culture but are not capable of glycosylating the final protein. Proteins which are expressed in high-level bacterial expression systems characteristically aggregate in granules or inclusion bodies which contain high levels of the overexpressed protein. Such protein aggregates typically must be solubilized, denatured and refolded using techniques well known in the art. See Kreuger, et al. (1990) in *Protein Folding*, Gierasch and King, eds., pgs 136–142, American Association for the Advancement of Science Publication No. 89-18S, Washington, D.C.; and U.S. Pat. No. 4,923,967.

MPF-4 and CPF-4 can also be isolated from the spent culture medium of mitogen-stimulated PBL preparations or any cell line that produces them. In the case of human PBLs, the PBLs are isolated from the buffy coat of whole blood using any number of methods well known in the art. An example of one of the many published methods for preparing human PBLs is Singh et al., Purification and Biochemical Properties of a Human Honocyte Derived Growth Factor, *Proc, Natl, Acad. Ssci.* 85: 6374–6378, 1985. Once isolated, the PBL preparation is thoroughly washed in a balanced salt solution to remove any non-cellular material.

The PBL preparation is then seeded into a defined, serum-free growth medium containing a mitogen. The ordinarily skilled artisan will be readily aware of a wide variety of published and commercially available growth media suitable for culturing PBL preparations. Similarly, a number of mitogens capable of stimulating PBL activity are well known in the art. By way of illustration and not limitation, the following are examples of mitogens consistent with the subject invention: lipopolysaccharide (LPS), phytohemoagglutinin (PHA), Concanavalin A (ConA), zymozan, and certain antibodies directed at mitogenic determinants.

The PBL preparation is then cultured under appropriate conditions for a period of time to allow the formation of MPF-4 and CPF-4, usually one to several days depending on initial seeding density. Spent growth medium is then collected and separated from the cells either by filtration, centrifugation or some other method.

Regardless of the means used to produce MPF-4 or CPF-4, purification will be required. A great variety of protein purification techniques are well known in the art, many of which are suitable and readily apparent to the ordinarily skilled artisan in light of the novel teachings here disclosed. A basic text describing state of the art protein purification techniques is Janson and Ryden, *Protein Purification*, VCH Publishers Inc., New York 1989.

One particularly useful purification method was dicovered and consists of first loading the spent culture medium onto a reversed phase purification column. Such columns are well known in the art and may be purchased from numerous vendors incuding Pharmacia, BioRad, and Amicon. Upon interacting with the column, the protein of interest is eluted using an increasing linear gradient of an organic solvent in trifluoroacetic (TEA). The preferred organic solvent is acetonitrile, and the fractions containing MPF-4 and CPF-4 are found in the 30–50% acetonitrile portion of the gradient. The more preferred portion of the gradient is the 33–39% region.

The eluted proteins are then contacted with a heparin affinity resin. The ordinarily skilled artisan will readily realize that this step is best achieved in a column chromatography mode. Heparin affinity columns are commercially available from some of the same vendors mentioned above. In this step, the molecules of interest, both MPF-4 or CPF-4, bind to the heparin column and are eluted using an increasing linear salt gradient. The preferred salt is NaCl, and the portion of the gradient that is preferably collected is the 0.1–2.0M portion. The more highly preferred portion of the gradient to collect is the 0.7–2.0M portion.

The final step is to run the 0.7–2.0M eluate on a second reversed phase column and eluting with a linear acetonitrile gradient in TFA. The preferred gradient is 25–75% acetonitrile and 27–67% is more preferred. The column output is monitored for absorbance at 220 nm. The peak protein fractions are assayed for cellular antiproliferative activity (bioactivity). The earlier eluting peak showing bioactivity is CPF-4 and the later eluting bioactive peak is MPF-4.

The following examples are useful for guidance in the purification process and for understanding the invention These examples are for illustrative purposes only and are not meant to limit the invention in any way.

EXAMPLE 1

Peripheral Blood Leukocyte Cultures

Pooled buffy coats, prepared from healthy donor blood, was purchased from Interstate Blood Bank. A PBL cell preparation was isolated from the pooled buffy coats by using histopaque™ (Sigma Chemical Co.; St. Louis, Mo. 63178) gradient centrifugation at 4° C. The PBL preparation was washed in Hank's balanced salt solution (GIBCO; Grand Island, N.Y.) and plated at a density of $3\times10^6$ cells/ml (total volume 4 L) in serum-free, minimal essential medium (GIBCO; Grand Island, N.Y.) supplemented with 2 mM L-glutamine, non-essential amino acids, 0.8 mM D-glucose, 100 U/ml penicillin, 100 µg/ml streptomycin and 20 µg per ml lipopolysaccharide (Sigma Chemical Co.; St. Louis, Mo. 63178). The PBL preparation was incubated for 30 hours at 37° C. in 5% $CO_2$, 95% air. The spent culture medium was harvested and the PBLs were removed by filtration through 0.2 µm filter.

EXAMPLE 2

Purification of MPF-4 and CPF-4

Four liters of cell-free spent culture medium were acidified by adding 0.1% (v/v) TFA acid and then loaded directly onto a Reverse Phase C4-RP-304™ (250× 21.5 mm) semi-preparative column (BioRad, Richmond, Calif. 4804) at a flow rate of approximately 15 ml/min. The column was eluted with a linear gradient of 0 to 50% acetonitrile in 0.1% TFA over 40 min. and then for 10 minutes at 50% acetonitrile, 0.1% TFA. The flow rate was 15 ml/min. Approximately 50, 15 ml fractions were collected. The elution profile was monitored at 220 nm. and fractions that eluted with 33%–39% acetonitrile were collected and pooled (C4-pool).

EXAMPLE 3

Heparin-Affinity Chromatography

The C4-pool was further fractionated by heparin affinity chromatography on a Econo-pac™ 5 ml heparin-sepharose cartridge (Biorad, Richmond, Calif. 94804). The bound proteins were eluted by a linear gradient of 0 to 2.0M NaCl in phosphate buffer saline (PBS) at a flow rate of 2.0 ml/min. The proteins that eluted from the column were pooled into three fractions: (1) non-heparin binding (flow through), (2) low-affinity heparin binding (0 to 0.7M NACl), and (3) high-affinity heparin binding (0.7M to 2.0M NACl) fractions.

EXAMPLE 4

Reversed Phase Analytical HPLC

The high affinity heparin binding fraction (3) (0.7M to 2.0M NACl) was applied to a Vydac™ 0.46×10 cm C-4 HPLC column (The Marshall Co.; Worthington, Ohio 43085), previously equilibrated with 27% acetonitrile, 0.1% TFA. The column was eluted with a linear gradient of 27% acetonitrile to 67% acetonitrile in 0.1% TFA, over a 40 min period. Absorbance was monitored at 220 nm and peak protein fractions were collected manually. The peak fractions were then assayed for bioactivity according to Example 5. Two peaks demonstrated the ability to inhibit cell proliferation. Upon routine amino acid sequencing, the earlier-eluting, bioactive peak was found to be CPF-4, and the later-eluting, bioactive peak was found to be MPF-4.

EXAMPLE 5

Endothelial Cell Proliferation Inhibition Assay

Primary retinal capillary endothelial cell cultures were prepared in substantial accordance with the procedure described in Buzney et al., Retinal Vascular Endothelial Cells and Pericytes: Differential Growth Characteristics in vitro, *Invest. Opthalmol. Visual Sci.* 24: 470–483 (1983) and separated from contaminating cells as described in Voyta et al., Identification and Isolation of Endothelial Cells Based on their Increased Uptake of Acetylated-low density Lipoprotein, *J. Cell Biol*, 99: 2034–2040 (1981).

Alternatively, bovine heart endothelial cells were obtained (American Type Culture Collection; Rockville Md. 20852) for use in the assay. Irrespective of source, the endothelial cells were seeded into 24 well tissue culture plates at a cell density of 10,000 cells/well in Dulbecco's modified Eagle Medium (GIBCO; Grand Island, N.Y.) supplemented with 5% bovine serum albumin, 1% penicillin-streptomycin, 1% L-glutamine, and 20 ng/ml fibroblast growth factor. Immediately after seeding the cells, various amounts of PF-4 (Sigma Chemical Co.; St. Louis, Mo. 63178), MPF-4, or CPF-4 (isolated as describe in the above examples) were added to individual growth wells. MPF-4 and CPF-4 were tested at final concentrations ranging from 0.001 to 1 µg/ml. For comparison, native PF-4 was tested over a range of 0.001 to 3 µg/ml, and supplemented medium alone served as the negative control. The endothelial cell cultures were allowed to grow for four days at 37° C., 5% $CO_2$ in a humidified tissue culture incubator. The cultures were then harvested individually by trypsinization and counted using a Zm-Coulter Counter (Coulter Electronics. Inc.; Opa Locka Fla. 33054).

The results were plotted in FIG. 1, and each point on the graph represented the average of 4 data points; ie one growth well per data point. The results showed that PF-4 inhibited endothelial cell proliferation and had an $IC_{50}$ of approximately 800–1000 ng/ml (approximately 130 nM). These results correlated well with recent studies published on the antipoliferative activity of recombinant PF-4 (*Science, 247:* 77–79 (1990)). The data also showed that under identical conditions, both MPF-4 and CPF-4 were more potent inhibitors of endothelial cell proliferation. MPF-4 demonstrated an $IC_{50}$ of 30–50 ng/ml (approximately 7 nM), and CPF-4 showed an $IC_{50}$ of approximately 150 ng/ml (20 nM). The inhibitory concentration for MPF-4 is close to the physiological range of PF-4 found in human plasma (Id.).

We claim:

1. A method of inhibiting angiogenesis which comprises administering an effective amount of the a composition consisting essentially of modified platelet factor-4 (SEQ ID NO: 1).

2. A method of inhibiting angiogenesis which comprises administering an effective amount of the a composition consisting essentially of cleaved platelet factor-4 consisting of a protein having the amino acid sequence of SEQ ID NO: 1 having disulfide bonds to a second protein having the amino acid sequence of SEQ ID NO: 2, said disulfide bonds bridging Cys-20 of SEQ ID NO: 1 to Cys-10 of SEQ ID NO: 2 and Cys-36 of SEQ ID NO: 1 Cys-12 of SEQ ID NO: 2.

* * * * *

UNITED STATES PATENT AND TRADEMARK OFFICE
CERTIFICATE OF CORRECTION

PATENT NO. : 5,512,550

DATED : April 30, 1996

INVENTOR(S) : Shalley K. Gupta and Jai P. Singh

It is certified that error appears in the above-indentified patent and that said Letters Patent is hereby corrected as shown below:

<u>Column 9</u>

Claim 1, line 2, please delete "the".

Claim 2, line 2, please delete "the".
<u>Column 10,</u>
Claim 2, line 8, after NO:1 please add --to--

Signed and Sealed this

Third Day of September, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 54 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:1:

```
Ser  Gln  Val  Arg  Pro  Arg  His  Ile  Thr  Ser  Leu  Glu  Val  Ile  Lys  Ala
 1              5                        10                       15

Gly  Pro  His  Cys  Pro  Thr  Ala  Gln  Leu  Ile  Ala  Thr  Leu  Lys  Asn  Gly
               20                       25                       30

Arg  Lys  Ile  Cys  Leu  Asp  Leu  Gln  Ala  Pro  Leu  Tyr  Lys  Lys  Ile  Ile
          35                       40                       45

Lys  Lys  Leu  Leu  Glu  Ser
     50
```

( 2 ) INFORMATION FOR SEQ ID NO:2:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:2:

```
Glu  Ala  Glu  Glu  Asp  Gly  Asp  Leu  Gln  Cys  Leu  Cys  Val  Lys  Thr  Thr
 1              5                        10                       15
```